United States Patent [19]

Kumai et al.

[11] Patent Number: 5,093,515

[45] Date of Patent: Mar. 3, 1992

[54] FLUORINATED BENZOYL COMPOUNDS

[75] Inventors: Seisaku Kumai, Fujisawa; Osamu Yokokoji, Yokohama; Akihiro Tamaoki, Ichihara; Ryonosuke Yoshida, Katano; Yoshiyuki Murakami, Yawata, all of Japan

[73] Assignees: Asahi Glass Company Ltd., Tokyo; Katayama Seiyakusho Co., Ltd., Osaka, both of Japan

[21] Appl. No.: 507,242

[22] Filed: Apr. 10, 1990

Related U.S. Application Data

[60] Continuation-in-part of Ser. No. 476,578, Feb. 7, 1990, Pat. No. 5,068,449, which is a division of Ser. No. 229,425, Aug. 8, 1988, abandoned.

[30] Foreign Application Priority Data

Aug. 14, 1987 [JP] Japan ................... 62-201862
Apr. 15, 1988 [JP] Japan ................... 63-91609
Apr. 11, 1989 [JP] Japan ................... 1-89823

[51] Int. Cl.$^5$ .......................... C07C 229/00
[52] U.S. Cl. ...................... 560/43; 546/138; 560/51; 560/60; 560/493; 560/840
[58] Field of Search .......................... 560/43

[56] References Cited

U.S. PATENT DOCUMENTS 4,833,270 5/1989 Bitha et al. ................... 548/485

FOREIGN PATENT DOCUMENTS 228035 7/1987 European Pat. Off. .
300311 1/1989 European Pat. Off. .
321191 6/1989 European Pat. Off. .
342849 11/1989 European Pat. Off. .

OTHER PUBLICATIONS

*Zhurnal Obshchei Khimii*, vol. 32, No. 10, pp. 3131–3134, Oct. 1962.

*Primary Examiner*—Paul J. Killos
*Attorney, Agent, or Firm*—Oblon, Spivak, McClelland, Maier & Neustadt

[57] ABSTRACT

A 2-chloro-4,5-difluorobenzoyl compound of the formula:

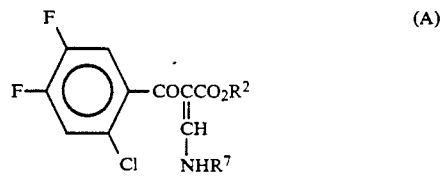

(A)

wherein $R^2$ is a lower alkyl group, and $R^7$ is a 2,4-difluorophenyl group or a 4-fluorophenyl group.

5 Claims, No Drawings

FLUORINATED BENZOYL COMPOUNDS

This is a continuation-in-part application of application Ser. No. 07/476,578 filed on Feb. 7, 1990, now U.S. Pat. No. 5,068,449 which is a division of application Serial No. 07/446,110 filed on Dec. 5, 1989 now U.S. Pat. No. 4,994,610 which is a division of application Ser. No. 07/229,425 filed on Aug. 8, 1988, now abandoned.

BACKGROUND OF THE INVENTION

1. Field of the Invention

The present invention relates to novel fluorinated benzoyl compounds useful as intermediates for medicines and agricultural chemicals, particularly as intermediates for fluorinated pyridone carboxylic acid type synthetic antibacterial agents.

2. Discussion of Background

It is known that 1,4-dihydro-4-oxoquinoline derivatives having cyclopropyl or a substituted aryl group at the 1-position (hereinafter referred to as quinolone compounds) are useful as fluorine-containing synthetic antibacterial agents. As intermediates for the synthesis of such antibacterial agents, the following intermediates have been proposed.

(1) Japanese Unexamined Patent Publication No. 74638/1983 discloses a synthesis of a quinolone compound having a cyclopropyl group at the 1-position and the intermediates for the synthesis thereof.

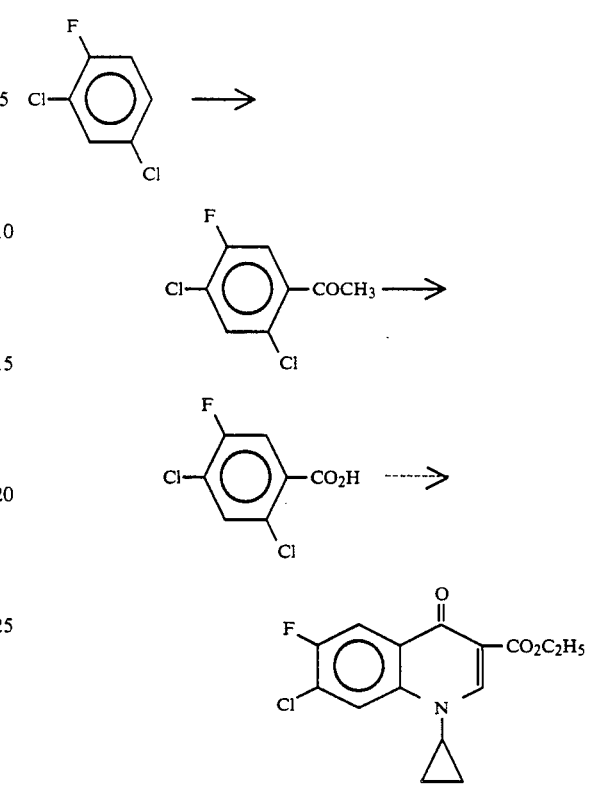

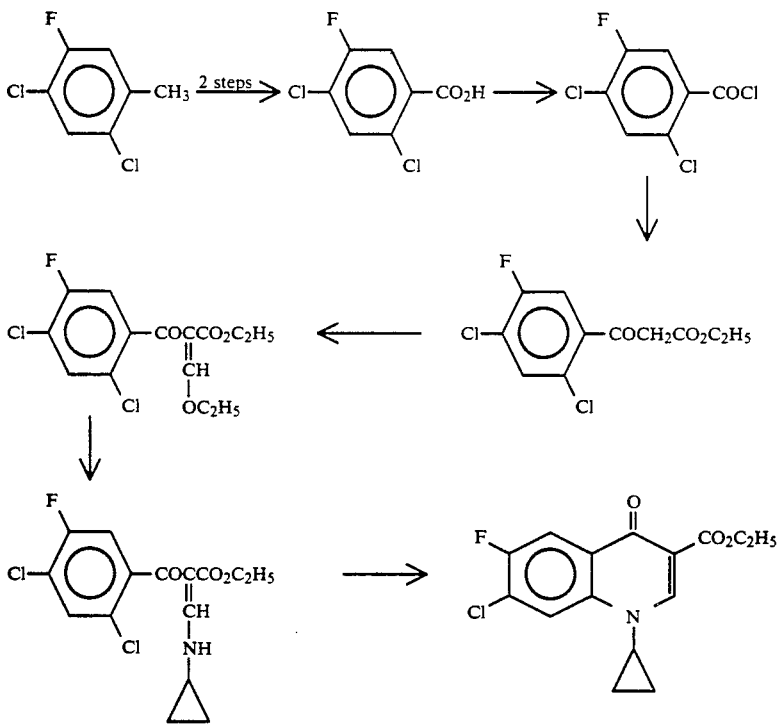

(2) Japanese Unexamined Patent Publication No. 85350/1986 discloses a synthesis of a quinolone compound via 2,4-dichloro-5-fluorobenzoic acid from 1,3-dichloro-4-fluorobenzene as the starting material.

(3) Japanese Unexamined Patent Publication No. 148484/1987 discloses a synthesis of a quinolone compound having a thienyl group at the 1-position from 2-bromo-4,5 difluorobenzoic acid.

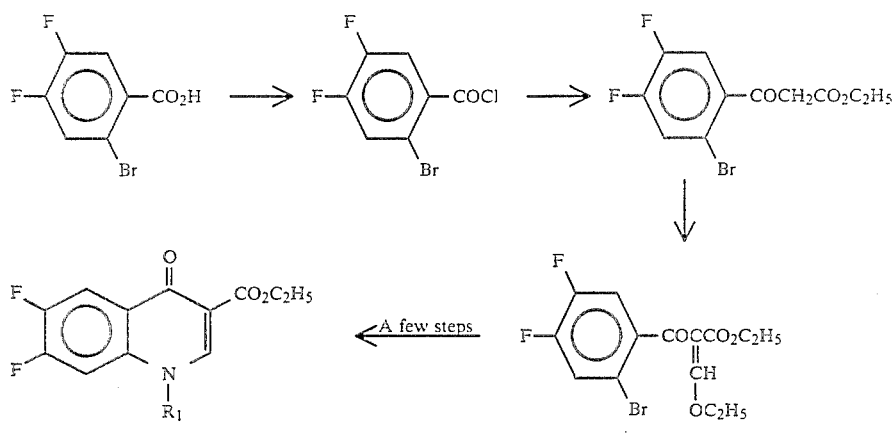

(R₁: thienyl group)

In both processes disclosed in publications (1) and (2), 7-chloroquinolone compounds are prepared via 2,4-dichloro-5-fluorobenzoic acid. Such 7 chloroquinolone compounds are reacted, usually after the hydrolysis, with a cyclic amine for conversion to various synthetic antibacterial agents, as shown below.

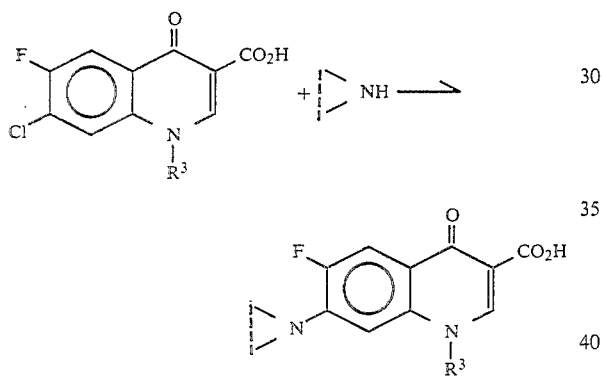

wherein $R^3$ is cyclopropyl, a substituted aryl group or a thienyl group.

However, the reactivity of chlorine at the 7-position of this quinolone compound derived from the chlorine at the 4-position of 2,4-chloro-5-fluorobenzoic acid is not high, and there is a drawback that the yield is inadequate, or the reaction condition is obliged to be severe even when the cyclic amine is a usual compound such as piperazine or a substituted piperazine.

Further, in the case of an amine compound having a low reactivity such as a tricyclic diazabicyclo alkyl compound as disclosed in Japanese Unexamined Patent Publication No. 103083/1987, it is preferred to employ highly reactive 7-fluoroquinolone compounds instead of the 7-chloroquinolone compounds having low reactivities.

The reactions of the 6,7-difluoroquinolone compound derived from 2-bromo-4,5-difluorobenzoic acid as shown in publication (3) with the cyclic amines proceed in good yield. However, this process has a drawback that 2-bromo-4,5 difluorobenzoic acid used as an intermediate in this process is difficult to synthesize. Namely, as a synthesis of 2-bromo-4,5-difluorobenzoic acid, Japanese Unexamined Patent Publication No. 108839/1987 discloses a hydrolysis method of 2-bromo-4,5-difluorobenzotrifluoride. However, by this method, 3,4-difluorobenzotrifluoride used as the starting material is hardly available and is difficult to synthesize. Further, this method has an additional disadvantage that an expensive corrosion-resistant material is required for the apparatus for the hydrolysis reaction.

Further, it is possible to obtain 2-bromo-4,5-difluorobenzoic acid by using known reactions, as shown below.

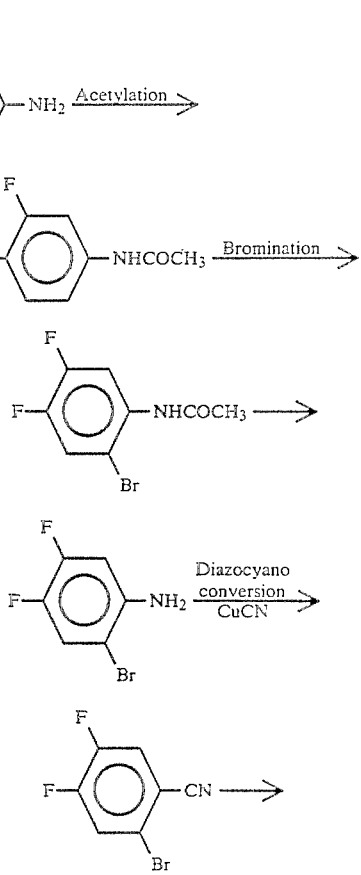

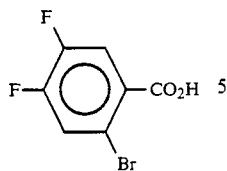

However, this method requires expensive 3,4-difluoroaniline as a starting material and employs highly toxic and dangerous copper cyanide. Therefore, it is difficult to practically operate this method on an industrial scale.

On the other hand, Japanese Unexamined Patent Publication No. 108839/1987 discloses a process represented by the following reaction as the only method for the production of 2-chloro-4,5-difluorobenzoic acid.

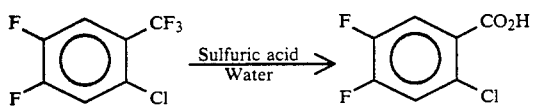

However, this process generates hydrogen fluoride, and accordingly has a drawback that the material of the reactor is obliged to be expensive such being disadvantageous for industrial operation.

If the novel compound of the present invention such as 2-chloro-4,5-difluoroacetophenone is employed, 2-chloro-4,5-difluorobenzoic acid can readily be produced by the following reaction without generation of such highly corrosive hydrogen fluoride. The process is advantageous for industrial operation.

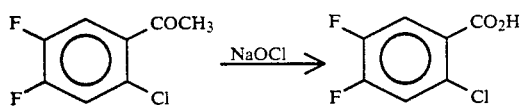

It is an object of the present invention to overcome the above-mentioned problems and to provide novel fluorinated benzoyl compounds useful as intermediates for fluorinated pyridone carboxylic acid type synthetic antibacterial agents.

SUMMARY OF THE INVENTION

The present invention provides a 2-chloro-4,5-difluorobenzoyl compound of the formula:

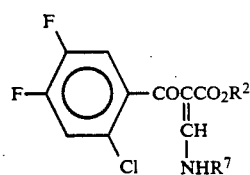
(A)

wherein $R^2$ is a lower alkyl group, and $R^7$ is a 2,4-difluorophenyl group or a 4-fluorophenyl group.

DETAILED DESCRIPTION OF THE PREFERRED EMBODIMENTS

Fluorinated benzoyl compounds as the starting materials of the present invention are represented by the following formula:

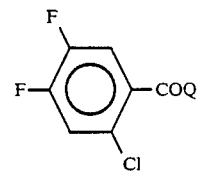
(1)

wherein Q is a lower alkyl group, a halogen atom, —CH$_2$CO$_2$R$^1$ wherein R$^1$ is a lower alkyl group, or

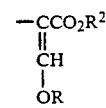

wherein each of $R^2$ and $R$ is a lower alkyl group.

The compound of the formula 1 wherein Q is a lower alkyl group may be represented by the following formula:

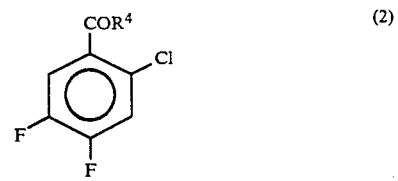
(2)

wherein $R^4$ is a lower alkyl group.

Specifically, the compound of the formula 2 includes the following compounds:
2-chloro-4,5-difluoroacetophenone ($R^4$=CH$_3$),
2-chloro-4,5-difluoropropiophenone ($R^4$=C$_2$H$_5$),
2-chloro-4,5-difluorobutylophenone ($R^4$=C$_3$H$_7$),
2-chloro-4,5-difluorovalerophenone ($R^4$=C$_4$H$_9$), and
2-chloro-4,5-difluorocaprophenone ($R^4$=C$_5$H$_{11}$).

These compounds can readily be converted to the corresponding benzoic acids by the following reaction, and can be led to quinolonecarboxylic acids useful as synthetic antibacterial agents by further a few steps of known reactions.

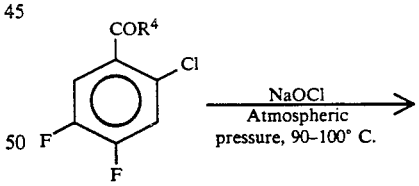

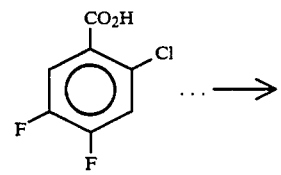

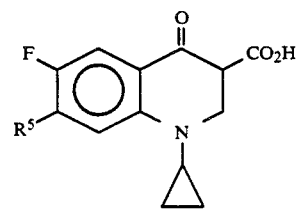

In the above formula, $R^4$ is preferably $CH_3$, and $R^5$ is preferably 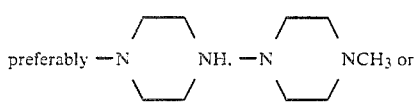

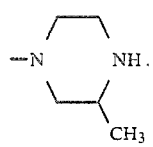

The compound of the formula 2, can readily be prepared by the following reaction.

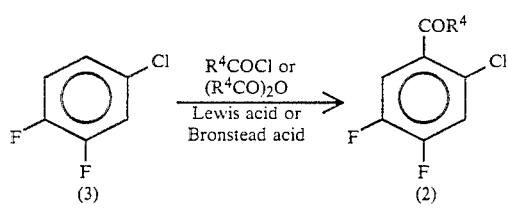

Namely, the compound of the formula 3, i.e. 1-chloro-3,4-difluorobenzene, is reacted with a carboxylic acid chloride such as acetyl chloride or with a carboxylic acid anhydride such as acetic anhydride in the presence of an acylating catalyst at a temperature of from 0° to 200° C., preferably from 10° to 150° C., followed by isolation by a usual method to obtain the compound of the formula 2.

The acylating catalyst may be a Lewis acid such as $AlCl_3$, $SbCl_5$, $FeCl_3$, $FeCl_2$, $TiCl_4$, $BF_3$, $SnCl_4$, $BiCl_3$, $ZnCl_2$ or $HgCl_2$ or a Bronstead acid such as HF, $H_2SO_4$, polyphosphoric acid, $CH_3SO_3H$, $CF_3SO_3H$, $FSO_3H$, p-$CH_3$-$C_6H_4$-$SO_3H$, $HClO_2$, $CF_3CO_2H$ or $HPOF_2$. The amount of the acylating catalyst is suitably selected within a range of from 0.1 to 500 mol%, preferably from 1 to 100 mol%, relative to 1-chloro-3,4-difluorobenzene.

The carboxylic acid chloride or the carboxylic acid anhydride is used usually in an amount of from 1 to 10 times, preferably from 1 to 2 times the theoretical amount required for the acylation of 1-chloro-3,4-difluorobenzene.

The reaction may be conducted in a solvent or without a solvent. The solvent is preferably nitrobenzene, carbon disulfide, dichloromethane, carbon tetrachloride or 1,2-dichloroethane. The reaction conditions such as the reaction temperature, the time and the pressure may suitably be selected. The reaction temperature is usually from 0° to 200° C., preferably from 10° to 150° C., the reaction time is usually from 0.5 to 10 hours, preferably from 1 to 4 hours. The reaction pressure is usually from 1 to 30 kg/cm², preferably from 1 to 5 kg/cm².

The compound of the formula 1 wherein Q is a halogen atom may be represented by the following formula 4, and the compound of the formula 1 wherein Q is $-CH_2CO_2R^1$ may be represented by the following formula 5.

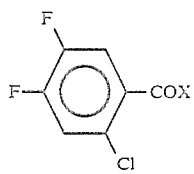

wherein X is a halogen atom.

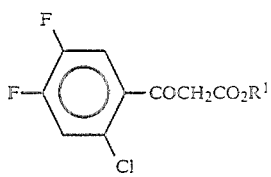

wherein $R^1$ is a lower alkyl group.

Specifically, the compound of the formula 4 includes 2-chloro-4,5-difluorobenzoyl chloride (X=Cl) and 2-chloro-4,5-difluorobenzoyl fluoride (X=F). Likewise, the compound of the formula 5 includes methyl 2-chloro-4,5-difluorobenzoylacetate ($R^1=CH_3$), ethyl 2-chloro-4,5-difluorobenzoylacetate ($R^1=C_2H_5$), propyl 2-chloro-4,5-difluorobenzoylacetate ($R^1=C_3H_7$) and butyl 2-chloro-4,5-difluorobenzoylacetate ($R^1=C_4H_9$).

The benzoyl halide compounds of the formula 4 can be readily prepared by the following reactions (a) and (b) from known 2-chloro-4,5-diflurorbenzoic acid.

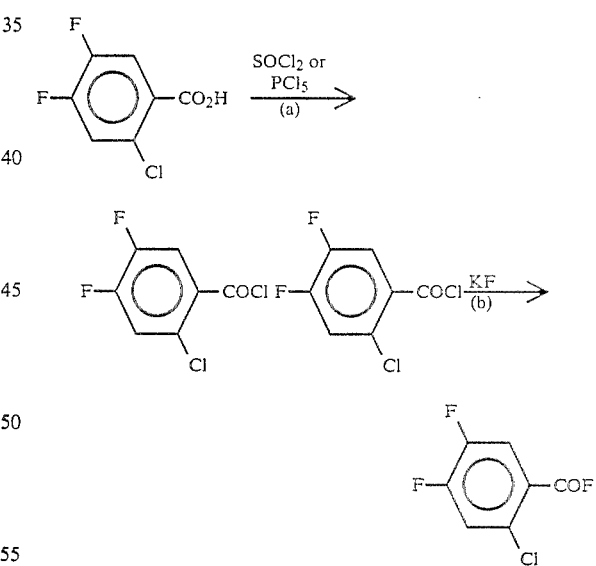

Whereas, the benzoylacetate compound of the formula 5 can readily be prepared by e.g. the following reactions (c) and (d).

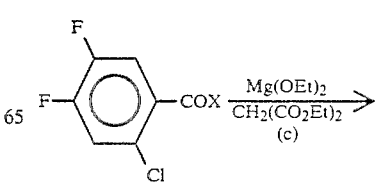

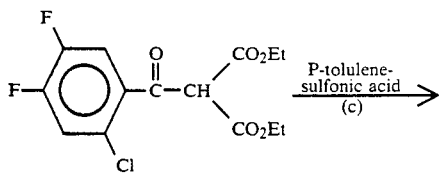 P-toluene-sulfonic acid (c) →

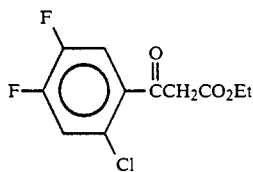

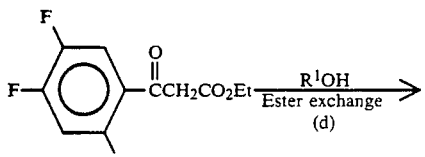 R¹OH / Ester exchange (d) →

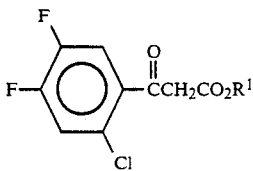

In the above formulas, "Et" may be not only the ethyl group but also other lower alkyl group.

The benzoyl acetate compound of the formula 5 can be led to a quinolone carboxylic acid useful as a synthetic antibacterial agent by employing a few steps of known reactions.

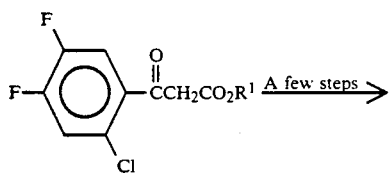 A few steps →

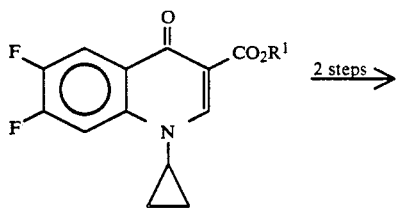 2 steps →

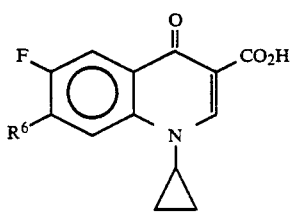

In the above formula, R⁶ is

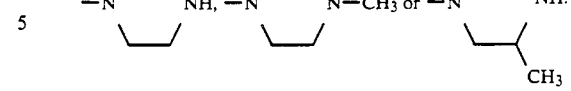

In the chlorination of the reaction formula (a), thionyl chloride, sulfuryl chloride, phosphorus pentachloride or phosphorus oxychloride may be used as the chlorinating agents. Among them, thionyl chloride is preferred. The chlorination may be conducted by reacting 2-chloro-4,5-difluorobenzoic acid with the chlorinating agent at a reaction temperature of from 50° to 80° C. in an aprotic polar solvent such as DMF, DMSO or dioxane, or without a solvent, followed by isolation by a usual method such as distillation to obtain 2-chloro-4,5-difluorobenzoyl chloride.

In the fluorination of the reaction formula (b), potassium fluoride is usually employed as the fluorinating agent. The fluorination is conducted usually at a reaction temperature of from 80° to 150° C. in the presence of an aprotic polar solvent such as sulforane, followed by isolation by a usual method such as distillation after the reaction to obtain 2-chloro-4,5-difluorobenzoyl fluoride.

The β-keto acid ester of the reaction formula (c) can be obtained by two step reactions. Namely, 2-chloro-4,5-difluorobenzoyl halide and diethyl malonate are reacted in the presence of magnesium ethylate to obtain diethyl 2-chloro-4,5-difluorobenzoylmalonate, which is then subjected to partial hydrolysis and decarboxylation in an aqueous medium at a reaction temperature of from 80° to 100° C. by using a catalytic amount of p-toluenesulfonic acid, to obtain the desired β-keto acid ester of ethyl 2-chloro-4,5-difluorobenzoyl acetate.

The first step of the reaction (c) will be described in further detail. Usually, magnesium ethylate is firstly prepared by the reaction of ethanol with magnesium metal. Further, a magnesium salt of diethyl malonate is formed in the system by reacting diethyl malonate and magnesium ethylate at a reaction temperature of from 30° to 60° C. in the presence of an aprotic solvent such as diethyl ether or toluene. Then, it is reacted with a 2-chloro-4,5-difluorobenzoyl halide at a reaction temperature of from −10° to −5° C., followed by acid treatment, solvent extraction, two phase separation, solvent removal by distillation etc. to obtain the desired diethyl 2-chloro-4,5-difluorobenzoylmalonate.

The ester exchange of the reaction formula (d) can readily be conducted by reacting a β-keto acid ethyl ester with an alcohol such as propanol or butanol at a reaction temperature of from 50° to 80° C. in the presence of an acid catalyst such as a catalytic amount of sulfuric acid or p-toluene sulfonic acid.

Further, the ester exchange may be conducted by hydrolyzing the β-keto acid ethyl ester with an alkali such as sodium hydroxide, followed by esterification with propanol or butanol in the presence of an acid such as sulfuric acid or hydrochloric acid.

The compounds of the formula 1 wherein Q is

may be represented by the following formula 6.

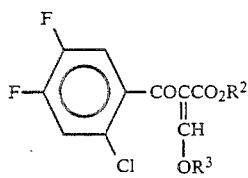

wherein each of $R^2$ and $R^3$ is a lower alkyl group.

The lower alkyl group for $R^2$ or $R^3$ includes methyl, ethyl, propyl and butyl.

Specifically, the compounds of the formula 6 includes methyl 2-(2-chloro-4,5-difluorobenzoyl)-3-methoxyacrylate, ethyl 2-(2-chloro-4,5-difluorobenzoyl)-3-ethoxyacrylate, propyl 2-(2-chloro-4,5-difluorobenzoyl)-3-propoxyacrylate and butyl 2-(2-chloro-4,5-difluorobenzoyl)-3-butoxyacrylate.

The compounds of the formula 6-can be prepared by reacting a compound of the formula 5 with an alkyl ortho-formate such as ethyl ortho-formate at a reaction temperature of from 100° to 150° C. in the presence of a reaction solvent such as acetic anhydride. After the reaction, acetic anhydride and unreacted ethyl ortho-formate are removed by distillation to obtain the compound of the formula 6 such as ethyl 2-(2-chloro-4,5-difluorobenzoyl)-3-ethoxyacrylate as the residue. Usually, the residue may be used directly for the subsequent step. The compounds of the formula 6 may be led to quinolone carboxylic acids useful as synthetic antibacterial agents by the following reactions.

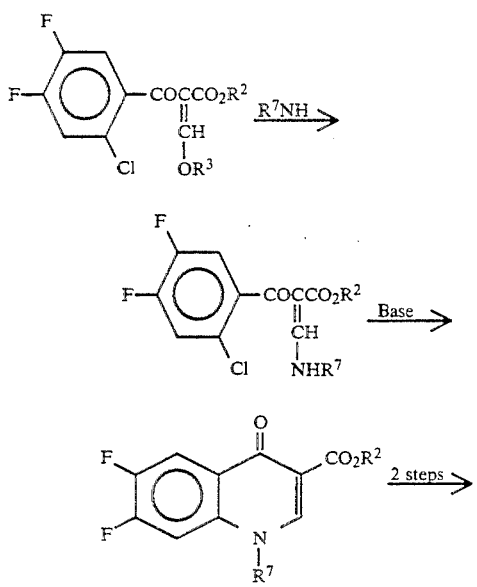

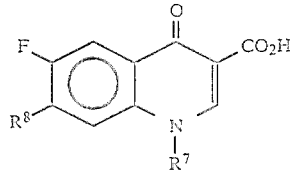

In the above formulas, $R^7$ is a 2,4-difluorophenyl group or a 4-fluorophenyl group, and $R^8$ is

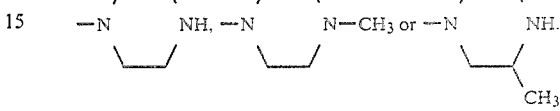

Now, the present invention will be described in further details with reference to Examples. However, it should be understood that the present invention is by no means restricted to such specific Examples.

REFERENCE EXAMPLE 1

Preparation of 2-chloro-4,5-difluoroacetophenone 23.6 g (0.3 mol) of acetyl chloride was added to a mixture comprising 29.7 g (0.2 mol) of 1-chloro-3,4-difluorobenzene and 40.0 g (0.3 mol) of aluminum chloride at a temperature of from 20° to 40° C. Then, the mixture was stirred at 120° C. for two hours. While still being hot, the mixture was poured on 250 g of ice, and the separated oil was extracted with ethylene chloride. The extract was neutralized and washed with water, and the solvent was distilled off under reduced pressure to obtain 31.2 g (yield: 82%) of 2-chloro-4,5-difluoroacetophenone. This compound was analyzed, and the analytical values were as follows. Boiling point: 65°–67° C./4–5 mmHg.

NMR analysis: $<^{19}F$-NMR$>$ $\delta$ppm from CFCl$_3$ $\delta$-129.9 ppm (d,d,d, $J_{p\text{-}p}$=22.7 Hz, $J_{p\text{-}M}$=9.6 Hz, $J_{p\text{-}H}$=10.8 Hz) $\delta$-137.3 ppm (d,d,d, $J_{p\text{-}p}$=22.7 Hz, $J_{F\text{-}H}$=7.3 Hz, $J_{p\text{-}H}$=10.3 Hz $<^1H$-NMR$>$ $\delta$ ppm from TMS $\delta$7.11–1.58 ppm (2H,m) $\delta$2.56 ppm (3H,s) $<$IR analysis$>$ 16595 cm$^{-1}$ (C=0).

REFERENCE EXAMPLE 2

Preparation of 2-chloro 4,5-difluorobenzoic acid

To 19.1 g (0.1 mol) of 2-chloro-4,5-difluoroacetophenone, 280.4 g (0.4 mol) of a 12% sodium hypochlorite aqueous solution was added, and the mixture was reacted under reflux for 4 hours. After cooling, concentrated hydrochloric acid was dropwise added thereto until the pH became 1. The formed white crystals were dissolved in methylene chloride and separated from the aqueous phase. The separated aqueous phase was extracted twice with methylene chloride, and the extracts were added to the oil phase. Then, the solvent was distilled off to obtain 16.4 g (yield: 85.1%) of 2-chloro-4,5-difluorobenzoic acid as white crystal.

REFERENCE EXAMPLE 3

Preparation of 2-chloro-4,5-difluorobenzoyl chloride

Into a 300 cc glass reactor, 100 g of 2-chloro-4,5-difluorobenzoic acid and 200 g of thionyl chloride were charged and stirred at about 60 to 70° C. for 3 hours.

Unreacted thionyl chloride was distilled off, and the residue was subjected to distillation under reduced pressure to obtain 101.8 g of 2-chloro-4,5-difluorobenzoyl chloride. The physical properties of the obtained 2-choloro-4,5-difluorobenzoyl chloride were as follows.

Boiling point: 93°-96° C./12-13 mmHg

NMR analysis: $<^{19}$F-NMR$>$ δ ppm, from CFCl$_3$ δ125.1 ppm (d.d.d., $J_{F-F}$=22.9 Hz, $J_{H-F}$=9.4 Hz, $J_{H-F}$=8.1 Hz) δ136.1 ppm (d.d.d., $J_{F-F}$=22.9 Hz, $J_{H-F}$=7.0 Hz, $J_{H-F}$=10.0 Hz) $<^1$H-NMR $>$ δ ppm from TMS δ7.37 ppm, δ8.03 ppm $<$IR analysis$>$ 1778 cm$^{-1}$ (C=0)

REFERENCE EXAMPLE 4

Preparation of 2-chloro-4,5-difluorobenzoyl fluoride

Into a 200 cc glass reactor equipped with a reflux condenser, 50 g of 2-chloro-4,5-difluorobenzoylchloride, 13.7 g of spray dried potassium fluoride and 100 g of sulforane were charged and reacted at 135° C. for 4 hours under stirring. After cooling, the inorganic salts were filtered off, and the residue was subjected to distillation under reduced pressure to obtain 42 g of 2-chloro-4,5-difluorobenzoyl fluoride. The physical properties of the obtained 2-choloro 4,5-difluorobenzoyl fluoride were as follows.

Boiling point: 72°-75° C./15 mmHg

NMR analysis: $<^{19}$F-NMR$>$ δ ppm from CFCl$_3$ δ-32.1 ppm(s), δ136.9 ppm (d.d.d., $J_{F-F}$=23.4 Hz, $J_{H-F}$=9.6 Hz, $J_{H-F}$=9.0 Hz), δ124.1 ppm (d.d.d., $J_{F-F}$=23.4 Hz, $J_{H-F}$=8.1 Hz, $J_{H-F}$=8.7 Hz) $<^1$H-NMR$>$ δ ppm from TMS 7.1 ppm(m)

REFERENCE EXAMPLE 5

Preparation of diethyl 2-chloro-4,5-difluorobenzoyl malonate

To 6.34 g of magnesium turnings, 13 cc of absolute ethanol and 1.2 ml of carbon tetrachloride were added, and the mixture was stirred After the initiation of the reaction, a solution comprising 39.9 g of diethyl malonate, 22 cc of absolute ethanol and 75 cc of toluene was dropwise added thereto at a temperature of from 50° to 70° C. After the dropwise addition, the mixture was stirred for two hours. Then, the reaction solution was cooled to −10° to −5° C., and a solution comprising 50 g of 2-chloro-4,5-difluorobenzoyl chloride and 15 ml of toluene was dropwise added thereto. Then, the mixture was stirred for two hours. A dilute sulfuric acid aqueous solution cooled with ice was added thereto, and the content was dissolved, subjected to phase separation and extracted three times with 60 cc of toluene. The organic phase was washed with water, then dried over anhydrous magnesium sulfate and concentrated to obtain 79.2 g of the desired product as a slightly yellow oily substance.

REFERENCE EXAMPLE 6

Preparation of diethyl 2-chloro-4,5-difluorobenzoyl malonate

The preparation of diethyl 2-chloro-4,5-difluorobenzoylmalonate was conducted in the same manner as in Example 5 except that 2-chloro-4,5-difluorobenzoyl fluoride was used as the starting material. As a result, 83.5 g of the desired compound was obtained from 50 g of 2-chloro-4,5-difluorobenzoyl fluoride.

REFERENCE EXAMPLE 7

Preparation of ethyl 2-chloro-4,5-difluorobenzoylacetate

To 70 g of diethyl 2-chloro-4,5-difluorobenzoylmalonate, 90 cc of water was added for emulsification. Then, 0.2 g of p-toluenesulfonic acid was added thereto, and the mixture was refluxed for three hours under vigorous stirring. After cooling, the reaction mixture was extracted three times with 150 cc of methylene chloride, and the extract was washed with a saturated sodium chloride aqueous solution, dried over anhydrous sodium sulfate, concentrated and then recrystallized from methylene chloride/n-hexane to obtain 32 g of the desired compound. The physical properties of obtained ethyl 2-chloro-4,5-difluorobenzoylacetate were as follows. From the results of the NMR analysis in chloroform d$_1$, this compound was found to be a mixture of a keto form and an enol-form.

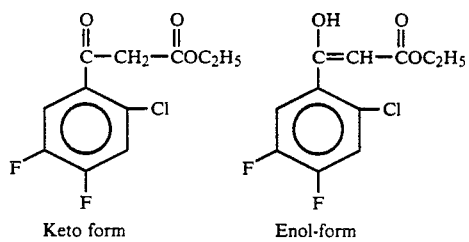

Keto form                Enol-form

Melting point: 48°-50° C.

Mass spectrum: parent peak 262

IR analysis: 3060-3120 cm$^{-1}$, 2850-2990 cm$^{-1}$, 1714-1739 cm$^{-1}$, 1450-1500 cm$^-$, 1130-1120 cm$^{-1}$ NMR analysis: $<^{19}$F-NMR$>$ δ ppm from CFCl$_3$ Keto form: δ129.0 ppm, δ132.3 ppm; Enol-form: δ137.5 ppm, δ138.5 ppm; $<^1$H-NMR $>$ δ ppm from TMS Keto form: δ7.3 ppm ($J_{H-F}$=9.4 Hz, $J_{H-F}$=6.7 Hz), δ7.6 ppm ($J_{H-F}$=8.3 Hz, $J_{H-F}$=10.0 Hz), δ4.0 ppm(s) δ4.2 ppm ($J_{CH2-CH3}$=7.08 ppm), δ1.26 ppm ($J_{CH2-CH3}$=7.08 ppm); Enol-form: δ7.3 ppm ($J_{H-F}$=9.4 Hz, $J_{H-F}$=6.7 Hz, δ7.5 ppm ($J_{H-F}$=8.3 Hz, $J_{H-F}$=10.8 Hz), δ5.62 ppm(s) δ4.3 ppm ($J_{CH2-CH3}$=7.1 Hz), δ1.35 ppm ($J_{CH2-CH3}$=7.1 Hz), δ12.5 ppm(OH).

REFERENCE EXAMPLE 8

Preparation of ethyl 2-(2-chloro-4,5-difluorobenzoyl)-3-ethoxyacrylate

Into a 200 cc glass reactor equipped with a stirrer, 26.3 g of ethyl 2-chloro-4,5-difluorobenzoylacetate, 23.7 g of ethyl ortho-formate and- . 40 ml of acetic anhydride were charged, and reacted at a reaction temperature of from 120° to 135° C. After completion of the reaction, the reaction mixture was concentrated by distillation under reduced pressure to obtain 31.5 g of the desired compound as the residue.

The obtained desired compound i.e. ethyl 2-(2-chloro-4,5-difluorobenzoyl)-3-ethoxyacrylate was analyzed, and the results were as follows. Further, as a result of the NMR analysis, this compound was found to be a mixture of an E-form and a Z-form.

Mass spectrum: M/z: 147, 175, 227, 255, 283, 318

NMR analysis: chloroform-d$_1$ solvent $<^{19}$F-NMR$>$ δ ppm from CFCl$_3$ δ132.1 ppm(m), 139.0 ppm(m) $<^1$H-NMR $>$ δ ppm from TMS δ1.11 ppm(t), $J_{CH2-CH3}$=7.20 Hz δ1.15 ppm(t), $J_{CH2-CH3}$=7.08 Hz δ1.32 ppm(t), $J_{CH2-CH3}$=7.08 Hz δ1.45 ppm(t), $J_{CH2-}$ $J_{CH_3}$=7.20 Hz δ4.13 ppm(q), $J_{CH_2-CH_3}$=7.08 Hz δ4.14 ppm(q), $J_{CH_2-CH_3}$=7.20 Hz δ4.21 ppm(q), $J_{CH_2-CH_3}$=7.08 Hz δ4.33 ppm(q), $J_{CH_2-CH_3}$=7.20 Hz δ7.68 ppm(s) δ7.81 ppm(s)

IR analysis: 1713 cm$^{-1}$ (C-C=O

1665 cm$^{-1}$ (-C=C-)

EXAMPLE 1

Preparation of ethyl 2-(2-chloro-4,5-difluorobenzoyl)-3-(4-fluoroanilino)-acrylate 25.5 g of acetic anhydride and 22.2 g of ethyl orthoformate were added to 26.3 g of ethyl 2-(2-chloro-4,5-difluorobenzoyl)-acetate, and the mixture was reacted for 2 hours under reflux. The reaction solution was concentrated under reduced pressure, and the oily residue thereby obtained was dissolved in 100 ml of ethanol. Then, 11.9 g of p-fluoroaniline was added thereto at room temperature, and the mixture was stirred for 5 hours. Precipitated crystals were collected by filtration. 29.9 g (78%). Melting point: 98°-102° C.

NMR analysis: Ethyl 2-(2-chloro-4,5-difluorobenzoyl)-3-(4-fluoroanilino)-acrylate $^{19}$Fnmr (δppm from R-11) 135.1 (d,d,d), 139.7 (d,d,d), 115.5 (d,d) $^1$Hnmr (δppm from TMS): In the brackets, isomers (E-form, Z-form) 12.68 ($^1$H,d, -NH-), 8.55(8.53) ($^1$H,d,-C=CH-) 6.99-7.35 (6H,m

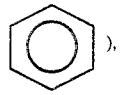

4.07(4.04) (2H,q,-CH$_2$CH$_3$) 1.06 (1.03 (3H,t,CH$_2$CH$_3$)

EXAMPLE 2

Preparation of ethyl 2-(2-chloro-4,5-difluorobenzoyl)-3-(2,4-difluoroanilino)-acrylate 12.8 g of acetic anhydride and 11.1 g of ethyl orthoformate were added to 13.1 g of ethyl 2-(2-chloro-4,5-difluorobenzoyl)-acetate, and the mixture was reacted for 2 hours under reflux. The reaction solution was concentrated under reduced pressure, and the oily residue thereby obtained was dissolved in 50 ml of ethanol. Then, 6.9 g of 2,4-difluoroaniline was added thereto at room temperature, and the mixture was stirred for 5 hours. Precipitated crystals were collected by filtration and washed with ethonol. 16g (80%), Melting point: 96.0°-111.5° C.

NMR analysis: Ethyl 2-(2-chloro-4,5-difluorobenzoyl)-3-(2,4-difluoroanilino)-acrylate $^{19}$Fnmr (δppm from R-11) 113.1 (d,d,d,d), 125.6 (d,d,d,d), 134.5 (d,d,d), 139.7 (d,d,d) $^1$Hnmr (δppm from TMS): 11.30 (1H,d,

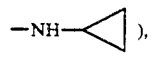

8.54 (1H,d,-C=CH-) 6.87-7.52 (5H,m

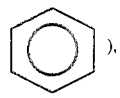

4.06 (2H,q,-CH$_2$CH$_3$) 0.95 (3H,t,-CH$_2$CH$_3$)

REFERENCE EXAMPLE 9

Preparation of ethyl 1-(4-fluorophenyl)-6,7-difluoro-1,4-dihydro-4-oxoquinolin-3-carboxylate 19.2 g of ethyl 2-(2-chloro-4,5-difluorobenzoyl)-3-(4-fluoroanilino)-acrylate was dissolved in 95 ml of dimethylformamide, and 8.3 g of potassium carbonate was added thereto. The mixture was heated for 60 minutes at a temperature of from 100° to 110° C. The reaction mixture was returned to room temperature and poured into water. Precipitated crystals were collected by filtration and washed with ethonol. 15.6 g (90%).

REFERENCE EXAMPLE 10

Preparation of ethyl 1-(2,4-difluorophenyl)-6,7-difluoro-1,4-dihydro-4-oxoquinolin-3-carboxylate Ethyl 2-(2-chloro-4,5-difluorobenzoyl)-3-(2,4-difluoroanilino)-acrylate was treated in the same manner as in Reference Example 9.

Yield: 92%.

The novel fluorinated benzoyl compounds of the present invention are useful as intermediates for medioines and agricultural chemicals, particularly as intermediates for fluorinated pyridone carboxylic acid type synthetic antibacterial agents. The intermediates of the present invention can be led to quinolone compounds having highly reactive fluorine at the 7-position. Accordingly, as compared with the conventional quinolone compounds having chlorine at the 7 position, the reactivity with a cyclic amine which is required to lead to a synthetic antibacterial agent, is high and it is thereby possible to obtain the desired synthetic antibacterial agent in good yield. Further, by virtue of this highly reactive fluorine, it is possible to obtain a synthetic antibacterial agent of the type which has not been obtained by the conventional method. Further, by using a novel compound of the formula 2 as the starting material, it is possible to obtain 2 chloro-4,5-difluorobenzoic acid more advantageously than the conventional methods.

What is claimed is:

1. A 2-chloro-4,5-difluorobenzoyl compound of the formula:

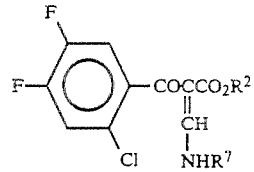

(A)

wherein R$^2$ is a lower alkyl group, and R$^7$ is a 2,4-difluorophenyl group or a 4-fluorophenyl group.

2. The compound of claim 1, wherein R$^7$ p$^t$ is a 2,4-difluorophenyl group.

3. The compound of claim 1, wherein R$^7$ is a 4-fluorophenyl group.

4. The compound according to claim 1, which is ethyl 2-(2-chloro-4,5-difluorobenzoyl)-3-(4-fluoroanilino)acrylate.

5. The compound according to claim 1, which is ethyl 2-(2-chloro-4,5-difluorobenzoyl)-3-(2,4-difluoroanilino)acrylate.

* * * * *